United States Patent [19]

Claud et al.

[11] Patent Number: 5,292,958
[45] Date of Patent: Mar. 8, 1994

[54] PROCESS FOR ELIMINATING THE DIETHANOLAMINE PRESENT IN TRIETHANOLAMINE AND PREPARATION PROCESS FOR PURIFIED TRIETHANOLAMINE

[75] Inventors: Gabrielle Claud, Paris; Alain Blanc, Saint Denis, both of France

[73] Assignee: Societe Francaise Hoechst, Puteaux, France

[21] Appl. No.: 968,315

[22] Filed: Oct. 29, 1992

[30] Foreign Application Priority Data

Oct. 29, 1991 [FR] France .................................. 91 13329

[51] Int. Cl.$^5$ ..................... C07C 209/84; C07C 209/86
[52] U.S. Cl. .................................... 564/499; 549/364; 562/567; 564/506; 564/497; 568/494
[58] Field of Search ............... 564/497, 498, 499, 506; 549/364; 568/494; 562/567

[56] References Cited

FOREIGN PATENT DOCUMENTS 1140867  1/1969  United Kingdom .

*Primary Examiner*—Glennon H. Hollrah
*Assistant Examiner*—Scott C. Rand
*Attorney, Agent, or Firm*—Browdy and Neimark

[57] ABSTRACT

Processes for eliminating the diethanolamine present in triethanolamine and the preparation of triethanolamine or compositions containing triethanolamine substantially free from diethanolamine in which the triethanolamine containing diethanolamine is treated with glyoxal in a molar ratio of glyoxal to diethanolamine greater than or equal to 1, then if desired the triethanolamine obtained or the composition containing it is isolated, and their use.

5 Claims, No Drawings

PROCESS FOR ELIMINATING THE DIETHANOLAMINE PRESENT IN TRIETHANOLAMINE AND PREPARATION PROCESS FOR PURIFIED TRIETHANOLAMINE

The present invention relates to a process for the elimination of the diethanolamine present in triethanolamine, its use and a preparation process for purified triethanolamine.

Currently, it is known that diethanolamine has, in certain cases, carcinogenic properties due to its chemical properties vis á vis nitrozation agents. In particular, this is the case for certain complex preparations containing diethanolamine intended for pesticidal or cosmetic compositions, or for obtaining cutting oils for which experiments on animals have shown their carcinogenic character. Consequently, the problem remains of eliminating the diethanolamine, also designated 2,2'-iminodiethanol, from the raw materials used to obtain these compositions and in particular the elimination of the diethanolamine present in triethanolamine, which is widely used in cutting oil formulations.

The triethanolamine obtained industrially by condensation of ethylene oxide with ammonia contains more or less significant quantities of diethanolamine. The boiling points of these two amines do not allow their perfect separation; consequently, even after being distilled, triethanolamine still often contains quantities greater than 0.1% by weight of diethanolamine, the elimination of which is recommended for certain uses in order to avoid the disadvantages mentioned previously.

Now, the Applicant has discovered a simple and efficient process for carrying out this elimination, and for obtaining triethanolamine free from diethanolamine.

The process according to the present invention is characterized by the fact that the triethanolamine containing diethanolamine is treated with glyoxal in a molar ratio of glyoxal to diethanolamine greater or equal to 1, then, if desired, the triethanolamine is isolated from the reaction medium by known means. The triethanolamine to be treated can be isolated, in a mixture or be included in a composition.

In the preferred operating conditions of the invention, the process described above is carried out in the following manner:

under an inert atmosphere,
at a temperature between 20° and 80° C.,
with a molar ratio of glyoxal to diethanolamine comprised between 1 and 2,
with glyoxal, either in aqueous solution at a concentration greater than 40% by weight, or in the form of the solid dihydrate trimer,
monitoring the elimination of the diethanolamine by regularly taking samples from the reaction medium in which samples the residual diethanolamine is ascertained, notably by analysis using gas phase chromatography.

The glyoxal is very active vis á vis the diethanolamine and it converts it very rapidly and quantitatively into N,N-bis (2-hydroxy ethyl) glycine. If desired, at the end of the reaction the triethanolamine can be isolated from the reaction medium, notably by distillation under reduced pressure. In this way pure triethanolamine is obtained.

It is known that triethanolamine oxidizes slowly in air turning coloured and releasing progressively in particular diethanolamine, formaldehyde and that the diethanolamine released also oxidizes slowly in air also giving coloured products. Consequently, the triethanolamine purified by the process of the invention must be stored either meticulously away from oxygen (KIRK-OTHMER, Encyclopedia of Chemical Technology, 3rd Edition, volume 1, New York, John Wiley and Sons, 1978, pages 944–950), or in the presence of an anti-oxidant or any other known means for inhibiting the effects of oxygen.

The process according to the invention allows triethanolamine to be obtained very easily containing less than 100 ppm by weight of diethanolamine starting from triethanolamine which can contain up to 2% by weight (20,000 ppm) of diethanolamine. At the end of treatment by the process according to the invention, pure triethanolamine can, if desired, be obtained for example by subjecting the reaction medium to distillation under reduced pressure.

Also a subject of the present invention is the use of the process described above to purify compositions containing triethanolamine with diethanolamine as an impurity.

Finally a subject of the present Application is a preparation process for triethanolamine substantially free from diethanolamine and for a composition containing triethanolamine substantially free from diethanolamine, characterized by the fact that the triethanolamine containing diethanolamine or the composition containing triethanolamine which contains diethanolamine is treated with glyoxal in a molar ratio of glyoxal to diethanolamine greater than or equal to 1, then the triethanolamine of the composition containing triethanolamine is isolated from the reaction medium.

The following examples illustrate the present Application without however limiting it. In these examples, the diethanolamine present in the triethanolamine was analyzed by gas phase chromatography according to the process described hereafter.

To analyze the diethanolamine present in the triethanolamine by gas phase chromatography, it is converted into its triacetylated derivative by the reaction of a known quantity of triethanolamine with 100 volumes of an acetic anhydride-pyridine mixture 20–80 by volume weighed exactly, for 30 minutes, at 80° C. in a closed vessel, then after cooling down to 20° C., 2 mg of methyl 3,4,5-trimethoxy benzoate is dissolved in the reaction medium which will serve as an internal standard and finally 1 ul of this solution is injected into the injector set at 250° C. of a gas phase chromatograph equipped with an ion trap detector (ITD), and a 25 metre capillary column of 0.25 mm diameter the internal covering of which is a film of polydimethylsiloxane with a thickness of 0.25 um, maintained isothermally at 1500° C., with a helium flow of 1 ml/min. Previously, the response coefficient of the triacetylated derivative of the diethanolamine was determined relative to the methyl 3,4,5-trimethoxy benzoate in the same conditions. The percentage by weight of the diethanolamine is calculated from the surface area of the the peaks of the diethanolamine and the standard and corrected by the weights of the test samples and by the response coefficient.

EXAMPLE 1

A mixture of 149.2 g (1 mole) of distilled triethanolamine containing 0.35% by weight of diethanolamine, i.e. 0.52 g (5 mmoles) with 1.45 g of a commercial aqueous solution of glyoxal at 40% by weight, i.e. 0.58 g (10 mmoles) of glyoxal is left for 24 hours at ambient temperature. In this way a solution of triethanolamine is obtained containing 0.007% of diethanolamine i.e. 0.10 mmole. This solution of triethanolamine can be used as it is to obtain a cutting oil formulation. If desired, distillation under reduced pressure of 0.3 mbar at 163° C. allows pure triethanolamine to be obtained with a quasi quantitative yield.

EXAMPLE 2

A mixture of 149.2 g (1 mole) of distilled triethanolamine containing 0.35% by weight of diethanolamine with 0.73 g of an aqueous solution of glyoxal at 40% by weight is left for 24 hours at 80° C. under an inert atmosphere. In this way a solution of triethanolamine containing 0.01% of diethanolamine i.e. 0.14 mmole is obtained after cooling the reaction medium down to ambient temperature.

EXAMPLE 3

A mixture of 149.2 g (1 mole) of distilled triethanolamine containing 0.35% by weight of diethanolamine with 0.36 g of an aqueous composition of glyoxal at 80% by weight i.e. 5 mmoles of glyoxal is left for 170 hours at 20° C. under an inert atmosphere. In this way triethanolamine containing 0.01% of diethanolamine is obtained.

EXAMPLE 4

A mixture of 149.2 g (1 mole) of distilled triethanolamine containing 0.35% by weight of diethanolamine with 0.55 g of an aqueous composition of glyoxal at 80% by weight i.e. 7.5 moles of glyoxal is left for 24 hours at 80° C. under an inert atmosphere. In this way triethanolamine containing 0.004% of diethanolamine is obtained.

We claim:

1. Process for the elimination of the diethanolamine present in triethanolamine wherein the triethanolamine containing diethanolamine is treated with glyoxal in a molar ratio of glyoxal to diethanolamine greater than or equal to 1.

2. Process according to claim 1, wherein the ratio of glyoxal to diethanolamine is comprised between 1 and 2.

3. Process according to claim 1 wherein said process is carried out at a temperature comprised between 20° C. and 80° C.

4. Process according to claim 1 wherein the glyoxal used is in aqueous solution of a concentration greater than 40% by weight.

5. Process according to claim 1 wherein the glyoxal used is in the solid dihydrate trimer state.

* * * * *